Dec. 16, 1969 C. G. KLEHM Plant Pat. 2,953
PEONY
Filed May 22, 1968
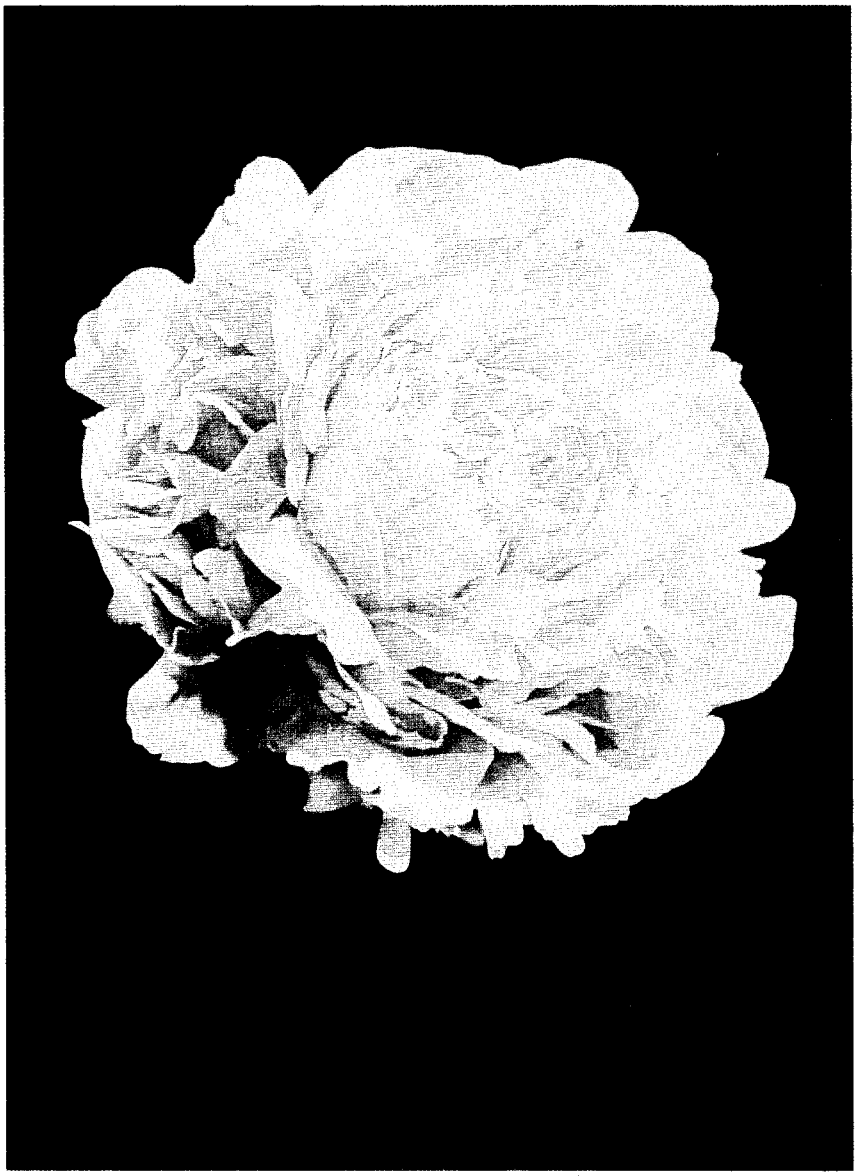
Inventor
Carl G. Klehm
By Hofgren, Wegner,
Allen, Stellman & McCord
Attys United States Patent Office Plant Pat. 2,953
Patented Dec. 16, 1969

2,953
PEONY PLANT

Carl G. Klehm, 3 E. Algonquin Road,
Arlington Heights, Ill. 60005

Filed May 22, 1968, Ser. No. 731,342
Int. Cl. A01h 5/02
U.S. Cl. Plt.—68 1 Claim The present invention relates to a new and distinct variety of peony plant of the genus Paeonia species *lactiflora*. Its uniqueness is characterized by an unusual coral pink flower petal color and smooth tailored petal arrangement of the normal blossom. The variety definitely possesses hybrid vigor because of its robust, clean growth and succulent, balanced root system.

This peony variety was originated by me at my nursery in Arlington Heights, Ill., in 1946. The pollen or male parent was a "bull" type seedling developed in my nursery and (not patented) kept for its ability to pass its vigorous growth and hardiness to its progeny. The pod or female parent was Mons. Jules Elie (not patented).

The hybridization was accomplished by hand pollination. The germinated seedling did not bloom until 1953 at which time it was selected from many other seedlings of the same cross. For the past 15 years it has been under strict and comparative observation during which time it has been propagated by asexual root division.

Although this peony plant derived its characteristics from random pairing of the genetic banks of both parents, its heterozygosity probably was inherited from the male parent. This vigor and health includes: clean, disease-free roots, stems and leaves; lush, deep green shoots, stems and foliage; a short and strong growth stature; and a balanced and vigorous root system. The pleasing coral pink flower with salmon color highlights is derived from the female parent, Mons. Jules Elie.

This particular peony plant is considered unique because of the hue of its flower petals, the healthy, fresh growth pattern and the over-all hybrid, vigorous appearance.

The size of the main flower is large, being 8–8½" in diameter under normal growth conditions. It has a full, double rose-type bloom with no stamens or carpels. Its blossom color is a pleasing coral pink with salmon highlights and a slight silver edging to the ventral petal side.

The variety is especially useful for garden and landscape purposes because of its stocky stiff stems which resist wind and rain. Its clean foliage makes a fine border or backdrop for flower plantings and because of its smooth bud and "opening in water after cutting" qualities, it is suitable for cutflower use.

The accompanying photograph shows a view of an individual flower in color as nearly true as reasonably possible in a color illustration of this character.

As a convenient summary, the following detailed description of this new peony plant is given with color terminology generally in accordance with The Royal Horticulture Society Color Chart, published in London, England, 1966 (except where general color terms are used).

Parentage:

*Seed parent.*—Mons. Jules Elie, from which this peony plant derives its beautiful flower color.

*Pollen parent.*—An unnamed seedling of the seed parent, developed in my nursery, from which the peony plant derives its hybrid vigor.

FLOWER

Blooming habit: Annually—considered mid-season.

Bud:

*Size.*—Large.
*Form.*—Smooth and round.
*Color.*—Pink—Fan 1, Plate 55C.
*Sepals.*—Smooth green with even edge.
*Calyx.*—Polysepalous.
*Peduncle.*—None.
*Opening.*—Easily with no splitting—a dependable performer.

Bloom:

*Size.*—Large—average expanded 8–8½" in diameter—normal conditions established plant.
*Borne.*—Singly, one main bud per stem with 3 to 5 axillary buds.
*Form.*—Rose type double with four to five rows of guard petals.
*Petalage.*—Double.
*Color.*—Coral Pink—Fan 1, Plate 55D—clear to "Neyron Rose."
*Variegations.*—None.
*Discolorations.*—None, although the intensity of the sun affects the amount of silver petal edging.

Petals:

*Texture.*—Thick—affected a little by weather.
*Appearance.*—Shiny and neat.
*Form.*—Smooth, slightly notched.
*Arrangement.*—Imbricated.
*Persistence.*—Above average.
*Fragrance.*—None.
*Lastingness.*—Above average.

Genital organs:

*Stamens, anthers.*—None, complete petaloidy.
*Stamens, filaments.*—None.
*Pollen.*—None.
*Styles, stigmas, ovaries.*—None.

Fruit: None.

PLANT

Form: Bush.
Growth: Healthy, strong and vigorous.

Foliage:

*Leaflets.*—Five to six.
*Size.*—Large.
*Quantity.*—Average.
*Color.*—Dark Green—Fan 3, Plate 136B.
*Shape.*—Elliptically acute.
*Stem.*—Stout, strong, 26–32" tall.
*Leaf stem.*—Thick and succulent.
*Texture.*—Dorsal is glossy with pronounced veins.
*Edge.*—Smooth.
*Serration.*—None.
*Stipules.*—None.
*Disease resistance.*—Resistant to leaf blotch and other bacterial peony diseases as observed for many years at my nurseries at Arlington Heights, Ill. and Barrington, Ill.

I claim:

1. A new and distinct variety of peony plant characterized by its flower color, growth habit and root structure as shown and described herein.

No references cited.

ROBERT E. BAGWILL, Primary Examiner